United States Patent [19]

Zhadanov

[11] Patent Number: 5,067,946
[45] Date of Patent: Nov. 26, 1991

[54] INJURY RESISTANT NEEDLE DEVICE

[76] Inventor: Semen Zhadanov, 101 Prospect Park, Metuchin, N.J. 08840

[21] Appl. No.: 507,247

[22] Filed: Apr. 10, 1990

[51] Int. Cl.$^5$ .............................................. A61M 5/32
[52] U.S. Cl. .................... 604/198; 604/192; 604/272
[58] Field of Search ............... 604/192, 198, 263, 272, 604/264, 164, 197, 110

[56] References Cited

U.S. PATENT DOCUMENTS

| | | | |
|---|---|---|---|
| 4,664,654 | 5/1987 | Strauss | 604/198 |
| 4,832,696 | 5/1989 | Luther et al. | 604/198 |
| 4,908,023 | 3/1990 | Yuen | 604/198 |
| 4,909,795 | 3/1990 | Gelabert | 604/198 |

Primary Examiner—C. Fred Rosenbaum
Assistant Examiner—Kathleen A. Doley
Attorney, Agent, or Firm—Ilya Zborovsky

[57] ABSTRACT

An injury resistant needle device comprises an outer protective tube, a needle unit having a needle which is movable relative to the outer protective tube between an extended position in which the needle is exposed outside of the outer protective tube and a retracted position in which the needle is completely confined inside the outer protective tube, and elements for moving the needle unit relative to the outer protective tube between the extended and retracted positions. The moving elements including a plurality of first engaging formations provided on the needle unit, and a rotary member provided with second engaging formations interengageable with the first engaging formations and turnable by a user, so that upon turning of the rotary member by a user's finger the needle unit is displaced between the extended and retracted positions.

5 Claims, 1 Drawing Sheet

INJURY RESISTANT NEEDLE DEVICE

BACKGROUND OF THE INVENTION

The present invention relates to injury resistant needle devices for blood connection, intravenous use, etc.

Needles for blood collection and for intravenous use are widely utilized. After respective operations of blood collection or intravenous use, there is a possibility of injuring of personnel by the exposed end of the needle. In order to prevent such an injury many devices have been designed to cover the needle end after the use. It is believed to be clear that further improvements of such designs are possible and desirable.

SUMMARY OF THE INVENTION

Accordingly, it is an object of the present invention to provide an injury resistant needle device which is a further improvement over the existing devices.

In keeping with these objects and with others which will become apparent hereinafter, one feature of the present invention resides, briefly stated, in a needle device which has an outer protective tube and a needle movable relative to said outer protective tube between a retracted position in which it is hidden in said outer protective tube and an extended position in which it is withdrawn from said outer protective tube to perform respective medical manipulations, and means for moving said needle between said retracted and extended positions and including a plurality of interengaging formations provided on said needle and a rotatable member provided with further engaging formations engageable with the engaging formations of said needle, said rotatable member being rotatable by a user's finger in two lateral directions so as to move the needle to the extended position or to the retracted position.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figures 1, 2:
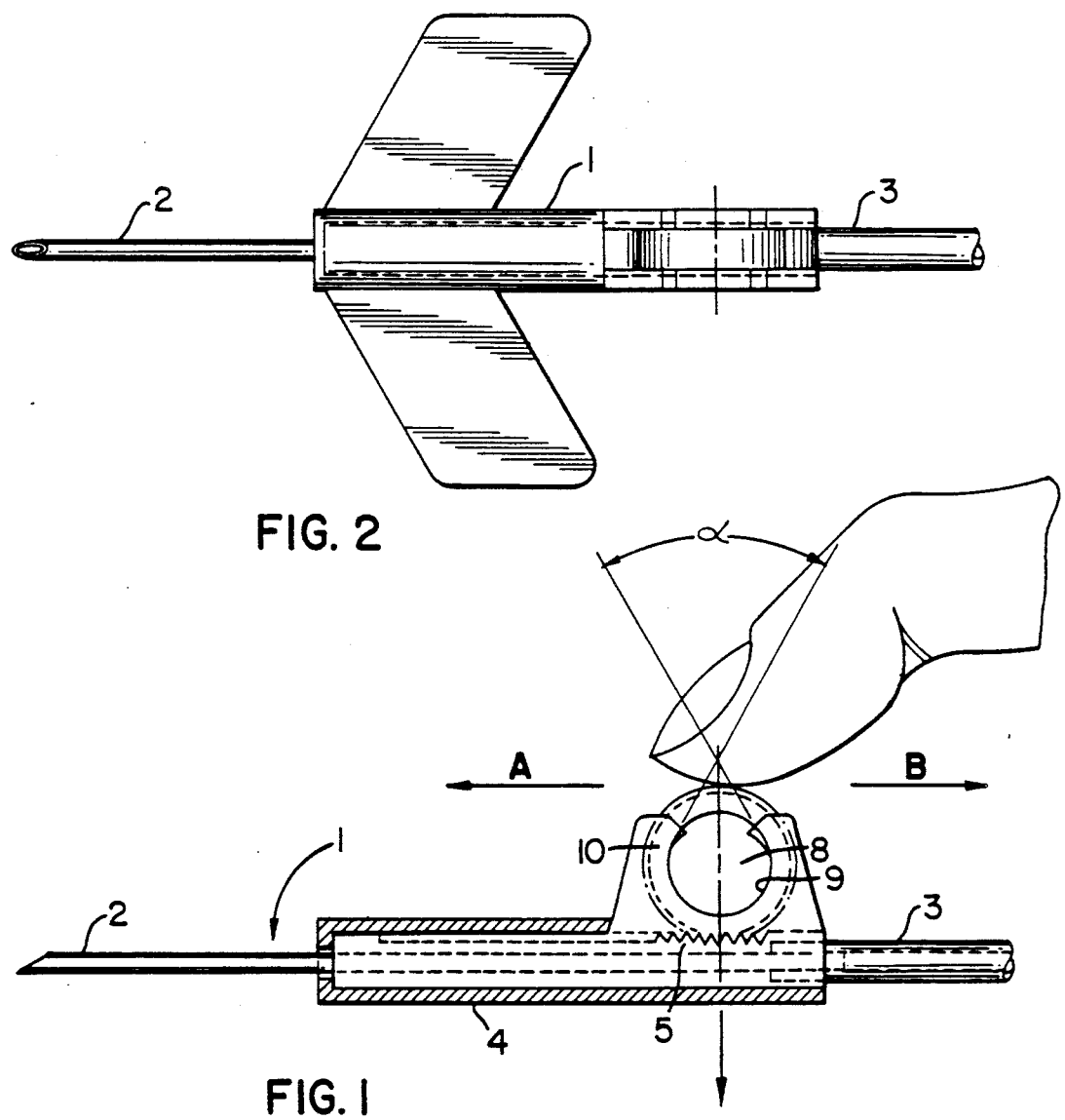
FIG. 1 is a side view of an injury resistant needle device in accordance with the present invention.
FIG. 2 is a plan view of the injury resistant needle device of FIG. 1.

An injury resistant needle device in accordance with the present invention has a needle unit which is identified as a whole with reference numeral 1. The needle unit 1 includes a needle 2 which is held with an inner tubular member 3. The needle device in accordance with the present invention is further provided with an outer protective tube identified with reference numeral 4. The outer protective tube 4 has an inner opening through which the tubular member 3 with the needle 2 can move between an extended position shown in the drawings and a retracted position which is not shown in the drawings and in which the needle 2 is completely inserted in the protective tube 4.

Means for moving the needle unit 1 between the extended position and the retracted position is further provided. The moving means includes a plurality of engaging formations identified with reference numeral 5 and provided on the inner tubular member 3. The engaging formations 5 can be formed as a plurality of teeth. The moving means further include a rotary member 6 which can be formed as a small wheel with a plurality of teeth 7 engageable with the teeth 5 of the inner tubular member 3. The shaft 8 of the wheel 6 extends through a transverse opening 9 in two upstanding flanges of the outer protective tube 2.

The user contacts with his finger the upper portion of the wheel 6 and turns it in a clockwise direction or a counterclockwise direction. Since the teeth 7 of the wheels 6 engage with the teeth 5 of the inner tubular member 3, the needle unit 1 is moved in a direction of the arrow B or in a direction of the arrow A. When the needle unit is moved in the direction of the arrow B it is retracted from its exposed position to the position in which the needle 2 is completely hidden in the protective tube 2. When the needle unit is moved in the direction of arrow A, the needle 2 is exposed for respective operations such as a blood collection or intravenous use.

The needle unit 1 can be locked so that it cannot displace longitudinally. The locking can be performed in the following manner. The shaft 8 can move upwardly and downwardly in the opening 9 of the outer protective tube. For turning the wheel 6, the wheel 6 is pressed by the user's finger downwardly so that its teeth 7 engage with the teeth 5 of the inner tubular member 3. After the use when the needle unit 1 is moved so that the needle 2 is located inside or outside of the protective tube, the finger pressure P is released. The shape of the teeth is selected so that in the pressureless position, the wheel 6 jumps upwardly but still in engagement of the teeth 7 and the teeth 5 of the inner tubular member. The opening 9 has an upper widened portion 10 which permits such upward jumping of the wheel 6.

The opening 9 has an upper mouth with side surfaces inclined at an angle α. When the wheel 6 is displaced upwardly, the outer surface of the shaft 8 of the wheel is clamped between side surfaces of the widened portion 10 of the opening 9 and the shaft and therefore the wheel cannot rotate any longer. Thus, the needle unit cannot displace longitudinally. This is used during the medical procedures, for example during insertion of the needle into a blood vessel, during which insertion the needle is reliably retained blocked and cannot displace backwards. The angle is selected to provide the above clamping.

For the above mentioned upward jumping of the wheel, the teeth of the wheel and the needle unit must be designed correspondingly. They must have for example correspondingly inclined flanks. With such correspondingly inclined flanks, the working pressure applied by the needle during its insertion for example into a blood vessel and acting in direction of the arrow B, produces on the inclined flanks a sufficient force component which acts vertically upwardly and displaces the wheel upwardly.

The invention is not limited to the details shown since various modifications ans structural changes are possible without departing in any way from the spirit of the invention.

What is desired to be protected by Letters Patent is set forth in the appended claims.

I claim:

1. An injury resistant needle device, comprising an outer protective tube; a needle unit having a needle which is movable relative to said outer protective tube between an extended position in which said needle is exposed outside of said outer protective tube and a retracted position in which said needle is completely confined inside the outer protective tube; and means for moving said needle unit relative to said outer protective tube between said extended and retracted positions, said moving means including a plurality of first engaging formations provided on said needle unit, and a rotary member provided with second engaging formations interengageable with the first engaging formations and turnable by a user, so that upon turning of said rotary member by a user's finger said needle unit is displaced between said extended and retracted positions.

2. A needle device as defined in claim 1, wherein said needle unit has an inner tube which holds said needle, said first engaging formations being formed on said inner tube.

3. A needle device as defined in claim 1; and further comprising means for preventing inadvertent movement of said needle unit between said retracted and extended positions.

4. A needle device as defined in claim 3, wherein said rotary member has a shaft, said outer protective tube having an opening with a flange for receiving said shaft, said opening, said flange, and said shaft forming said preventing means, said opening and said flange being formed so that when a pressure is applied by a user to said rotary member toward said needle unit said rotary member displaces toward said needle unit but when the pressure is released said rotary member is displaced away of said needle unit and is clamped in said flange of said opening so that it cannot rotate and therefore said needle unit cannot move between said positions.

5. A needle device as defined in claim 4, wherein said opening has side surfaces against which said shaft is clamped.

* * * * *